United States Patent [19]

Kabbe et al.

[11] Patent Number: 4,757,072
[45] Date of Patent: Jul. 12, 1988

[54] CARCINOSTATIC AGENT

[75] Inventors: Hans-Joachim Kabbe, Leverkusen; Robert Bierling, Wuppertal, both of Fed. Rep. of Germany; Ghanem Atassi, Brussels, Belgium

[73] Assignee: Bayer Aktiengesellschaft, Leverkusen, Fed. Rep. of Germany

[21] Appl. No.: 26,800

[22] Filed: Mar. 17, 1987

[30] Foreign Application Priority Data

Apr. 4, 1986 [DE] Fed. Rep. of Germany ....... 3611194

[51] Int. Cl.⁴ .......................................... A61K 31/505
[52] U.S. Cl. .................................................. 514/257
[58] Field of Search ......................................... 514/257

[56] References Cited
PUBLICATIONS

Chemical Abstracts, 89:146805a, (1978).

*Primary Examiner*—Jerome D. Goldberg
*Attorney, Agent, or Firm*—Sprung Horn Kramer & Woods

[57] ABSTRACT

A carcinostatic composition useful in inhibiting the growth of colon and/or rectal tumors comprising 8-amino-12-oxo-10, 12-dihydroindolo [1,2-b]-quinazoline of the formula:

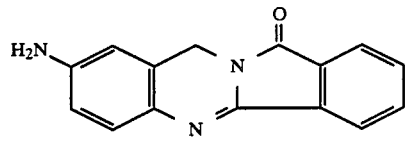

2 Claims, No Drawings

CARCINOSTATIC AGENT

It is known that polycyclic compounds which are substantially flat can have antibacterial or carcinostatic actions because they are often able to intercalate between the turns of the DNA helix [L. S. Lerman, Proc. Nat. Acid. Sci. USA 49 94 (1963)]. We had suspected that compounds which can be obtained from diamines and anhydrides also have a so-called intercalating action of this type [H. J. Kabbe, Liebigs Ann. Chem. 1978, 398]. In fact, however, on investigation in a series of tumour test models, for example leukaemia 1210, B 16 melanoma or Lewis lung carcinoma, these substances proved to be virtually inactive.

It has now been found that one of the compounds which we previously synthesised, 8-amino-12-oxo-10,12-dihydroisoindolo[1,2-b]quinazoline (I) shows excellent tumour-inhibiting properties in the model of colon 38 carcinoma in the mouse. This model is representative of the action against cancer of the colon and rectum in humans.

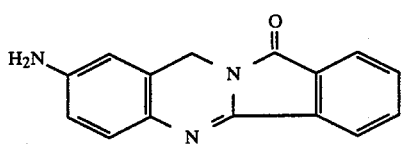

This result has to be denoted extremely surprising since an action against the colon tumour has to date been disclosed for only very few compounds. Thus, to date, essentially only 5-fluorouracil, which acts as an antimetabolite, has been used for the palliative treatment of these tumours.

In particular, the action on this specific tumour exhibited by compounds which are known to have an intercalating action is, as a rule, zero or only marginal. The discovery of high activity against colon 38 carcinoma is thus to be regarded as an important advance in the area of cancer. It is a particularly remarkable fact that as few as two oral administrations result in a complete cure.

The synthesis of the active substance (I) is indicated in the said publication (see above). In the examples which follow, the tumour-inhibiting property of I with respect to colon 38 carcinoma, and the absence of a colon 38 action with ellipticine as comparison substance, are described.

The active compound can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compounds should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, physiological sodium chloride solution (1 percent strength), non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavour-improving agents or colorants in addition to the abovementioned auxiliaries.

In special cases rectal administration may also be advantageous.

In the case of parenteral administration, solutions of the active compounds, employing suitable liquid vehicles, can be used.

In general, it has proved advantageous, in the case of parenteral administration, to administer amounts of about 0.1 to 10 g, preferably about 0.2 to 5 g per kg of body weight per day to achieve effective results, and in the case of oral administration, the dosage is about 0.1 to 20, preferably 0.2 to 10, g per kg of body weight per treatment day.

Treatment can be effected either once to thrice a day or at greater intervals, for example once a week.

Nevertheless, it can at times be necessary to deviate from the amounts mentioned, and in particular to do so as a function of the body weight of the experimental animal or of the nature of the administration method, but also because of the species of animal and its individual behaviour towards the medicament, or the nature of the formulation of the medicament and the time or interval over which the administration takes place. Thus it can suffice in some cases to manage with less than the abovementioned minimum amount, whilst in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

EXAMPLE 1

On day 0, 70 mg of colon 38 tumour tissue from C57BL6 mice were implanted subcutaneously into the axillary region of B6C3F1 mice (10 animals for each dose and 20 animals as controls). On days 2 and 9 after tumour implantation, compound I was administered intraperitoneally (as a 2 percent suspension in 1 percent sodium chloride solution with the addition of about 1%

Tween 80). On day 20, the tumour weights of the treated and untreated mice were compared.

The following result was obtained:

| Dose (mg/kg) | Mean tumour weight per mouse after 20 days | |
|---|---|---|
| | in mg | in % of the controls |
| 200 (a) | 0 | 0 |
| 100 (b) | 0 | 0 |
| 50 (c) | 307 | 32 |
| controls | 936 | 100 |

Of the treated 10 animals in each group it was possible to classify as completely cured the following numbers: 9 in each of a and b, and 2 in c; no signs of toxicity related to the substance occurred in any treatment group.

EXAMPLE 2

200 mg of active substance (I) were dissolved in 1 ml of 1n hydrochloric acid, and the solution was diluted with 9 ml of sterile water and then administered intraperitoneally. The experiment procedure was analogous to that in Example 1.

| Dose (mg/kg) | Mean tumour weight per mouse after 20 days | |
|---|---|---|
| | in mg | in % of the controls |
| 100 | 0 | 0 |
| 50 | 252 | 28 |
| controls | 900 | 100 |

6 of the 10 animals treated with 100 mg/kg were completely cured. No signs of toxicity related to the substance occurred in either group.

EXAMPLE 3

Treatment was effected orally instead of intraperitoneally. The substance was administered as a suspension on days 2 and 9, exactly as in Example 1. The tumour weights were determined on day 20.

| Dose (mg/kg) | Mean tumour weight per mouse after 20 days | |
|---|---|---|
| | in mg | in % of the controls |
| 800 (a) | 0 | 0 |
| 600 (b) | 0 | 0 |
| 400 (c) | 2 | 0 |
| 200 (d) | 221 | 27 |
| controls | 798 | 100 |

Of the 10 animals treated in each group, the following numbers were classified as completely cured: 9(a), 8(b), 5(c) and 1(d). No signs of toxicity related to the substance were recorded.

EXAMPLE 4

(comparison)

B6C3F1 mice were implanted with colon 38 tumour tissue in analogy to Example 1. Treatment was effected with 200 mg ellipticine/kg [as a 2 percent suspension in 1 percent sodium chloride solution with the addition of about 1% Tween 80] on days 2 and 9 (intraperitoneally), with evaluation on day 20. Neither cures nor a reduction of the tumour weight compared with the controls were observed.

What is claimed is:

1. A method of combating or inhibiting carcinoma of the colon and/or rectum comprising administering to a patient having a carcinoma of the colon and/or rectum a therapeutically effective amount for inhibiting carcinoma of the colon and/or rectum of the therapeutic composition comprising 8-amino-12-oxo-10,12-dihydroisoindolo[1,2-b]-quinazole.

2. A therapeutic composition in customary tablet, capsule, coated tablet, pill, granule, aerosol, syrup, emulsion or parenteral solution formulation form useful in the treatment of carcinoma of the colon and/or rectum comprising a therapeutically effective amount for inhibiting carcinoma of the colon and/or rectum of 8-amino-12-oxo-10,12-dihydroisoindolo[1,2-b]-quinazoline and an inert, non-toxic, pharmaceutically suitable vehicle or solvent.

* * * * *